United States Patent [19]

Huxley et al.

[11] 4,275,218
[45] Jun. 23, 1981

[54] SULFOLENE HYDROGENATION

[75] Inventors: Edward E. Huxley; Martin E. Nash, both of Borger, Tex.

[73] Assignee: Phillips Petroleum Company, Bartlesville, Okla.

[21] Appl. No.: 168,886

[22] Filed: Jul. 14, 1980

[51] Int. Cl.³ .......................................... C07O 333/48
[52] U.S. Cl. ..................................................... 549/87
[58] Field of Search ........................................... 549/87

[56] References Cited

U.S. PATENT DOCUMENTS

| | | | |
|---|---|---|---|
| 2,451,298 | 10/1948 | Morris et al. | 549/87 |
| 3,322,686 | 5/1967 | Brown et al. | 252/432 |
| 3,928,385 | 12/1975 | Huxley | 549/87 |

Primary Examiner—Alan Siegel

[57] ABSTRACT

A process for converting sulfolene compounds to sulfolane compounds comprising contacting at least one sulfolene compound with hydrogen in the presence of a metal hydrogenation catalyst and an effective amount of ammonia as an $SO_2$ neutralizer or scavenger. The addition of ammonia increases conversion of sulfolene to sulfolane, improves product color, and reduces polymer formation during hydrogenation. In a preferred embodiment, the ammonia is admixed with the hydrogen prior to contacting with the sulfolene compound.

10 Claims, No Drawings

SULFOLENE HYDROGENATION

This invention relates to an improved process for the catalytic hydrogenation of sulfolene compounds. In accordance with another aspect, this invention relates to a process for the hydrogenation of sulfolene compounds in the presence of ammonia. In accordance with a further aspect, this invention provides a method for neutralizing excess sulfur dioxide and other sulfur compounds present in sulfolene feeds for hydrogenation to sulfolane by the addition of ammonia. In a further aspect, the hydrogenation of sulfolene can be carried out in the additional presence of a tertiary amine.

Sulfolane compounds are saturated five-membered rings of four carbon atoms and a sulfur atom, the latter having two oxygen atoms directly attached thereto. The structural formula of sulfolane itself, the simplest unsubstituted sulfolane compound, is

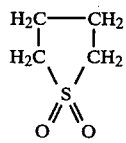

Sulfolane, i.e., 2,3,4,5-tetrahydrothiophene-1,1-dioxide, is especially valuable as a selective solvent. Another especially widely used sulfolane compound is 2,4-dimethylsulfolane which has also been used as a selective solvent to separate aromatic hydrocarbons from petroleum fractions. Other uses for sulfolane compounds are in pesticidal compositions and intermediates in the production of various organic chemicals.

Sulfolane compounds are generally prepared by reaction of sulfur dioxide with a conjugated diene to form a sulfolene compound which is then catalytically hydrogenated to form the sulfolane compound. Sulfur dioxide is always present in the sulfolene compound, either as residual starting material or as product from the chemical equilibrium existing between sulfolene compounds and their respective precursors, and must be removed prior to the hydrogenation step since it acts as a catalyst poison. Several methods have been proposed to remove the excess sulfur dioxide before hydrogenation. These methods are generally described in U.S. Pat. Nos. 3,928,385; 3,622,598; 3,544,430; 3,514,469; 3,417,103; 3,152,144; 3,077,479 and 2,451,298. All of these methods exhibit various disadvantages, such as use of expensive, highly reactive and corrosive treating agents, use of liquid and solid treating agents which must subsequently be removed from desired product, etc.

Accordingly, an object of this invention is to provide an improved process for the hydrogenation of sulfolene.

Another object of this invention is to provide SO₂ neutralizer or scavenger material effective for improving hydrogenation of sulfolenes to sulfolanes.

A further object of this invention is to provide a material that effectively neutralizes residual sulfur-containing compounds in sulfolene feeds so as to increase conversion, improve product quality, and reduce polymer formation during hydrogenation.

Other objects, aspects, and the several advantages of this invention will become apparent to one skilled in the art upon reading this disclosure and the appended claims.

In accordance with the invention, a process is provided which comprises contacting at least one sulfolene compound with hydrogen in the presence of a metal hydrogenation catalyst and an effective amount of ammonia under hydrogenation conditions sufficient to effectively convert sulfolene compounds to sulfolane compounds.

In accordance with one embodiment of the invention, ammonia is admixed with the hydrogen prior to contacting of the sulfolene compounds and hydrogenation catalysts.

In accordance with another embodiment of the invention, hydrogenation of sulfolene to sulfolane is carried out in the presence of ammonia and a tertiary amine.

The present invention provides a method for hydrogenating sulfolene compounds to sulfolane compounds with high retention of catalyst activity and high product quality by adding ammonia to the hydrogenation zone.

The term "sulfolene compound" as employed herein defines generically the unsubstituted and substituted unsaturated compounds comprising or containing a sulfolene nucleus, i.e., a five-membered ring of four carbon atoms and a sulfur atom with a single olefinic linkage between two adjacent carbon atoms of said ring, and two oxygen atoms each of which is directly attached to said sulfur atom. Thus, the generic term "a sulfolene compound" covers the unsubstituted and substituted sulfolenes, viz, the 3-sulfolenes having the general structure

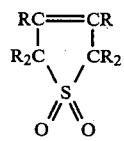

and the 2-sulfolenes having the structure

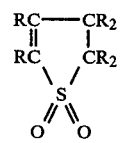

wherein each R is individually selected from the group consisting of hydrogen, hydrocarbon radicals, heterocyclic radicals, and inorganic radicals and combinations thereof which do not interfere with the hydrogenation reaction. Those compounds wherein each R is individually selected from the group consisting of hydrogen and hydrocarbon radicals having one to eight carbon atoms are presently preferred. Suitable hydrocarbon radicals include alkyl, aryl, cycloalkyl, and combinations thereof.

The following representative sulfolene compounds are suggested to those skilled in the art as being operable in this invention: 3-sulfolene, 2-sulfolene, 3-methyl-2-sulfolene, 2-methyl-3-sulfolene, 3-methyl-3-sulfolene, 2,4-dimethyl-2-sulfolene, 2,4-dimethyl-3-sulfolene, 3-ethyl-3-sulfolene, and their homologues, as well as other sulfolene compounds, and admixtures thereof.

Similarly, the term "sulfolane compound" as used herein refers to a hydrogenated sulfolene compound, which may be either substituted or unsubstituted. The structure formula of the sulfolane compounds therefore, is

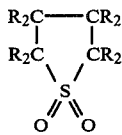

wherein R is as defined hereinabove, with at least one R on each of two adjacent carbon atoms being hydrogen.

Catalysts which can be used in this invention include any of those known in the art useful in the catalytic hydrogenation of sulfolenes to sulfolanes. A preferred class of hydrogenation catalysts are those which comprise the base metal hydrogenation catalysts, such as those containing or consisting of nickel, cobalt, copper, platinum, palladium or mixtures of these metals with themselves or with other metals such as iron, zinc, chromium, cadmium, etc. These metals may be used in finely divided form such as, for example, Raney nickel or may be suitably supported on a support such as kieselguhr, aluminum oxide, diatomaceous earth and the like. The catalyst can be charged in increments or all at once. Generally 1 to 10 weight percent catalyst based on the amount of sulfolene compound present is employed.

The catalytic hydrogenation is preferably carried out with the sulfolene compound in the liquid state, for example, by maintaining it above its melting point (but below its thermal decomposition temperature) or in solution in a suitable solvent such as water, benzene, dioxane, alcohols, such as methyl, ethyl, isopropyl or tertiary butyl alcohol, the sulfolane compound itself, and the like. The amount of solvent used can vary and generally will be in the range of about 5 to about 60 weight percent, preferably about 15 to about 40 weight percent of total solvent-sulfolene mixture. The use of a solvent permits better control over the temperature of the rapid and exothermic hydrogenation reaction.

Tertiary amines can be employed in the process of the present invention, if desired. Suitable tertiary amines are generally described in U.S. Pat. No. 3,928,385 which is incorporated herein by reference. Specific examples include trimethylamine, triisobutylamine, N-methyldiethylamine, tridodecylamine, N-methyl-N-ethylpropylamine, N,N-dimethylbutylamine, N-ethyldipropylamine, triphenylamine, tribenzylamine, tri-p-tolylamine, tricyclohexylamine, N,N,N',N'-tetramethylethylenediamine, triethylenediamine, etc., and mixtures thereof.

Hexamethylenetetramine, the presently preferred tertiary amine, is a colorless, odorless and crystalline compound with the formula $(CH_2)_6N_4$.

Hexamethylenetetramine is also known by the following: 1,3,5,7-tetra-azatricyclo(3,3,1,1$^{3.7}$)decane; methenamine; hexamethyleneamine; hexamine; formin; aminoform and urotropin. It is soluble in water, chloroform, methyl alcohol and ethyl alcohol.

The tertiary amine will generally be employed in an amount in the range of from about 0.05 to about 2 weight percent based on the sulfolene compound to be hydrogenated. It is desirable that the teritary amine be admixed with the sulfolene feed prior to contacting the feed with the catalyst.

The amount of ammonia employed can vary widely, depending, for example, on the amount of sulfur dioxide present in the sulfolene compound. Generally, however, ammonia in the hydrogen stream ranging from one part per million (ppm) to about one weight percent based on the total hydrogen plus ammonia stream can be employed. A preferred range of ammonia in the hydrogen stream is from about 10 ppm to about 1000 ppm. It is desirable that the ammonia be admixed with the hydrogen feed prior to contacting with the sulfolene compound and catalyst.

The reaction temperatures and pressures can vary and be carried out over wide ranges. In fact, any temperature is operable at which the reaction mixture is liquid and which is below that at which the materials decompose. We prefer to operate in the range from about 40° C. to about 70° C. and at a hydrogen pressure in the range from about 70 kPa to about 3500 kPa or higher and requiring from about one to about six hours for the hydrogenation reaction to be completed.

Following completion of the hydrogenation reaction, the sulfolane product can be recovered by conventional procedures. Generally, this comprises first cooling the reaction mixture, venting gases therefrom, filtering the cooled reaction mixture to remove the catalyst and fractionating the filtered reaction mixture to remove solvent and unreacted sulfolene compound.

Though we do not wish to be bound by theory, it appears to us that the ammonia, by being preferably mixed with the hydrogen prior to entering the hydrogenation zone, is better dispersed for rapid reaction with the sulfur dioxide than other methods employing solid or liquid treating agents. High localized concentrations of ammonia, resulting in reaction of ammonia with sulfolene compound to form amino-substituted sulfolane compounds, are also avoided. It also appears that the inventive process provides for more efficient basification of the catalyst surface than prior art methods.

The following examples are presented in further illustration of the invention and should not be construed in undue limitation thereof.

EXAMPLE 1

The following inventive and comparative runs demonstrate the hydrogenation of 3-sulfolene to sulfolane over Raney nickel catalyst in the presence or absence of ammonia in the hydrogen stream.

The 3-sulfolene employed in these runs was a commercial batch prepared from 1,3-butadiene and sulfur dioxide and containing approximately 33 percent by weight of water. The aqueous 3-sulfolene solution was treated with 0.005 weight percent of aqueous hydrogen peroxide (30 weight percent $H_2O_2$) and maintained at 60° C. for one hour to destroy excess sulfur dioxide originally present as reactant. The thus-treated aqueous 3-sulfolene solution contained approximately 50–100 ppm sulfur dioxide, believed to result from decomposition of sulfolene.

The above-described 3-sulfolene solution (950 ml) was placed in a 2 liter reactor with Raney nickel (ca. 40 g). The vapor space was flushed with hydrogen (comparative run 1 containing no ammonia and inventive run 2 containing 20 ppm ammonia in the hydrogen stream) after which the reactor was pressurized to 2170 kPa with hydrogen (run 2 hydrogen contained 20 ppm ammonia). The reactor was heated at 60° C. with vigorous agitation for the specified time period. The liquid phase in the reactor was sampled periodically and analyzed by vapor phase chromatography. Results are recorded in the table.

Runs 3 and 4 were conducted as described for runs 1 and 2, respectively, with the additional use of hexamethylenetetramine (1 g) added to the sulfolene solution prior to addition of nickel catalyst. Results are recorded in the Table.

TABLE

| Run No. | NH$_3$ | HMTA[1] | Time, Min. | Conv. %[2] |
|---|---|---|---|---|
| 1 (Comp.) | No | No | 30 | 33.1 |
|  |  |  | 60 | 57.4 |
|  |  |  | 90 | 68.2 |
| 2 (Inv.) | Yes | No | 30 | 36.0 |
|  |  |  | 60 | 71.9 |
|  |  |  | 90 | 91.5 |
| 3 (Comp.) | No | Yes | 30 | 38.7 |
|  |  |  | 60 | 76.3 |
|  |  |  | 90 | 97.1 |
| 4 (Inv.) | Yes | Yes | 30 | 41.9 |
|  |  |  | 60 | 75.3 |
|  |  |  | 90 | 99.7 |

[1] Hexamethylenetetramine
[2] Percent conversion of 3-sulfolene to sulfolane.

Comparison of inventive runs 2 and 4 with comparative runs 1 and 3, respectively, leads one to the conclusion that the use of ammonia in the hydrogen stream results in higher conversion of 3-sulfolene to sulfolane at the end of the specified time period. These results further demonstrate that additional use of hexamethylenetetramine in the inventive process further increases the conversion of starting material to desired product.

The reasons for the lack of increased conversion at the 60 minute sampling of run 4 compared to that of run 3 are not well understood.

We claim:

1. A process for the production of a sulfolane compound which comprises contacting at least one sulfolene compound with hydrogen and a metal hydrogenation catalyst in the presence of an effective amount of ammonia under suitable hydrogenation conditions to convert said sulfolene compound to the corresponding sulfolane compound.

2. A process according to claim 1 wherein the ammonia is admixed with the hydrogen prior to contacting with the sulfolene compound and catalyst.

3. A process according to claim 1 wherein there is additionally present during said contacting a tertiary amine.

4. A process according to claim 3 wherein said tertiary amine is hexamethylenetetramine.

5. A process according to claim 1 wherein the amount of ammonia present ranges from 1 ppm to about 1 weight percent based on the total of hydrogen plus ammonia used.

6. A process according to claim 5 wherein the amount of ammonia present ranges from about 10 ppm to 1000 ppm.

7. A process according to claim 1 wherein said hydrogenation conditions comprise a temperature at which the reaction mixture is liquid and is below that at which the materials decompose and a hydrogen pressure ranging from about 70 kPa to about 3500 kPa.

8. A process according to claim 1 wherein said catalyst consists essentially of Raney nickel.

9. A process according to claim 2 wherein the amount of ammonia present ranges from 1 ppm to about 1 weight percent based on the total hydrogen plus ammonia, the temperature is in the range of about 40° C. to about 70° C., and there is additionally present during said contacting a tertiary amine.

10. A process according to claim 9 wherein said tertiary amine is hexamethylenetetramine.

* * * * *